United States Patent [19]
Eisner et al.

[11] Patent Number: 4,976,616
[45] Date of Patent: * Dec. 11, 1990

[54] DENTAL TRAY HANDLE SHIELD OR PROPHYLACTIC

[75] Inventors: Mark R. Eisner, Allentown; Charlton D. Becker, Emmaus, both of Pa.

[73] Assignee: Steri-Shield Products, Inc., Ivyland, Pa.

[*] Notice: The portion of the term of this patent subsequent to Oct. 11, 2005 has been disclaimed.

[21] Appl. No.: 229,242

[22] Filed: Aug. 8, 1988

[51] Int. Cl.$^5$ ............................................. A61G 15/00
[52] U.S. Cl. ........................................ 433/77; 433/79; 150/155
[58] Field of Search .................... 433/77, 79, 116; 206/63.5, 69, 368, 369; 118/504; 16/114 R, 116 A; 128/846, 856; 150/155; 74/551.8, 558.5

[56] References Cited

U.S. PATENT DOCUMENTS

| | | | |
|---|---|---|---|
| 4,559,671 | 12/1985 | Andrews et al. | 362/804 |
| 4,605,124 | 8/1986 | Sandel et al. | 16/114 R |
| 4,610,630 | 9/1986 | Betush | 433/79 |
| 4,777,574 | 10/1988 | Eisner | 362/399 |
| 4,795,669 | 1/1989 | Bowskill et al. | 362/804 |

Primary Examiner—Cary E. Stone
Attorney, Agent, or Firm—Sanford J. Piltch

[57] ABSTRACT

A dental tray handle protective covering, shield or prophylactic comprised of a thin, tear-resistant, semi-rigid but elastic material which is disposable for providing a covering or barrier for the entirety of each of several different types of dental tray which will significantly reduce and/or prevent the spread of disease through the continued touching of the dental tray handle by non-sterile gloved or ungloved hands of dental practitioners and others.

7 Claims, 1 Drawing Sheet

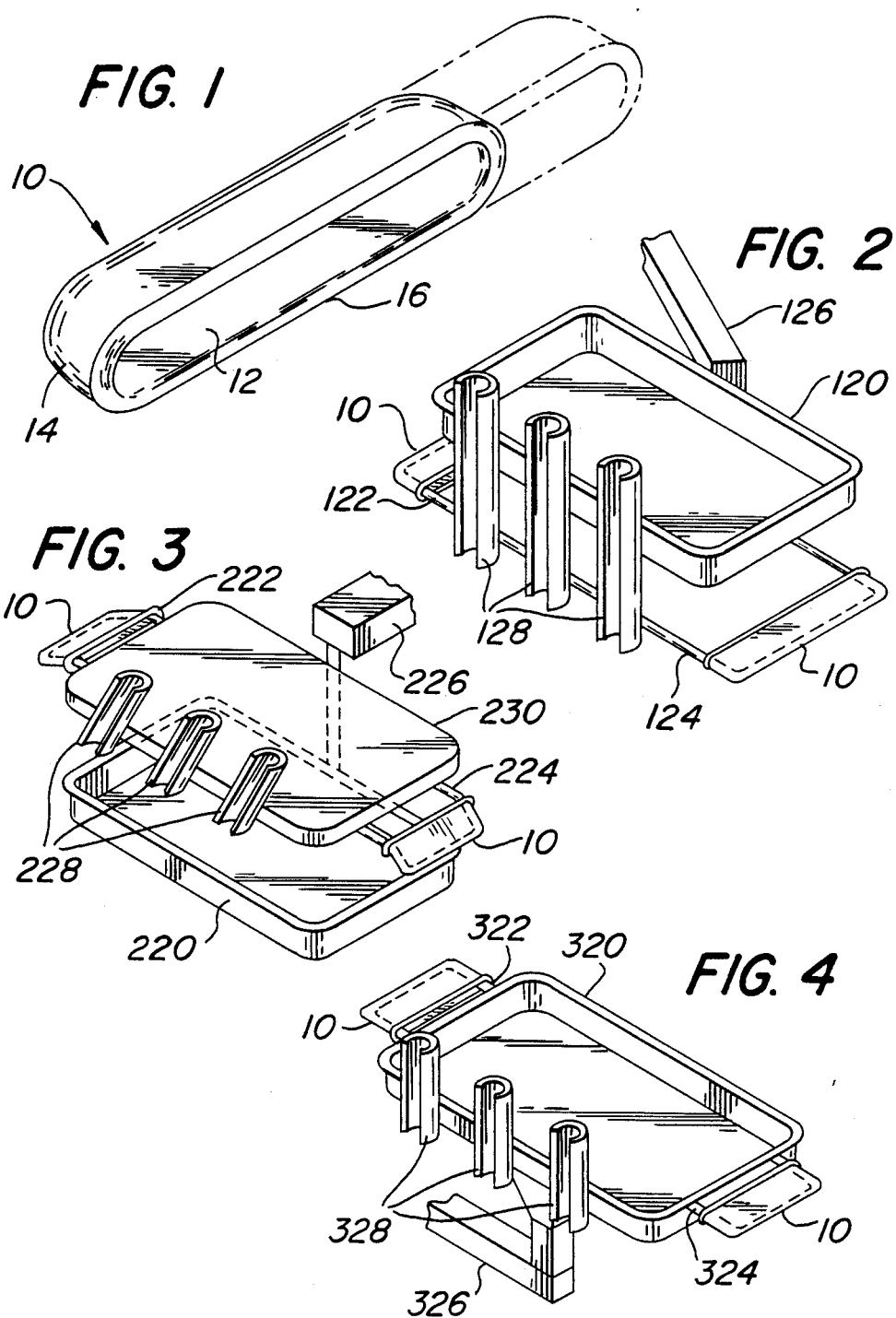

DENTAL TRAY HANDLE SHIELD OR PROPHYLACTIC

BACKGROUND OF THE INVENTION

Dental practitioners have been aware for years that the repeated touching of the dental tray or bracket table, or their handles, by gloved or ungloved hands after the dental practitioner's or the hygienist's hands have been in or around the mouths of several different patients without sterilization can bring about the spread of contagious diseases. Such contagious or communicable diseases are borne in or on the body fluids and/or tissues which become attached to the exterior surfaces of the gloved or ungloved hands of the dental practitioner or hygienist and are transmitted to the tray or bracket table handles or adjusting means through contact. More recently the spread of the Hepatitus virus and the Acquired Immune Deficiency virus have caused great concern for dental practitioners, hygienists and other dental office staff, not only for their patients, but also for their own health and well-being.

Both the Hepatitus virus and the Acquired Immune Deficiency virus are carried in or on body fluids and/or tissues. In the environment in which dental practitioners and hygienists work, i.e. inside the mouth, body fluids such as saliva, blood, etc. and the tissues comprising the gum and portions of the teeth, the pulp and root, may potentially transmit the virus through contact. The process of cleaning and/or repairing teeth by filling caries or performing a root canal procedure requires the drilling of the teeth and the subsequent scattering of tissue particles and body fluids about the mouth. Some of those particles and/or fluids become attached or adhere to the gloved or ungloved hand of the dental practitioner or hygienist. Cleaning and sterilizing the tray or bracket table handles or adjusting means between patients has been a serious problem for dental practitioners and hygienists because of their construction.

During dental procedures ranging from filling caries to cleaning teeth, the tray or bracket table is normally repositioned at least once as the dentist or hygienist repositions his or her body for a better view of the interior of a patient's mouth or to perform a particular procedure. The tray or bracket table handles or other adjusting means are touched by the dental practitioner or hygienist in attempts to place the tray or bracket table with its attached equipment and/or loose tools to a more desirable position for ease of access and use. Repositioning of the tray or bracket table is accomplished without the dental practitioner or hygienist sterilizing their gloved or ungloved hands while working on a patient. Anything they may have come into contact with while their hands were in the patients's mouth will be transmitted to the surface of the tray or bracket table, the tray handle or other adjusting means upon contact.

The dental tray or bracket table is not thought of as a disease transmission device. It is usually cleaned, but not sterilized. The sterilization of a dental tray or bracket table, which is large and cumbersome when not mounted to the dental chair frame and is not easily placed in a sterilization chamber as may be small dental instruments, is extremely difficult. The tray or bracket table may be sprayed with a disinfecting agent but such practice does not totally eliminate bacteria or virus. Although usually disinfected between patients, the disinfecting of the tray or bracket table certainly does not occur between hand contact with the tray or bracket table by the dental practitioner, hygienist or other staff members and the performing of dental procedures on a patient.

In recent years dental practitioners and hygienists have become increasingly aware of the rapid spread of communicable diseases through body fluids and tissues such as may be dislodged and/or become attached to the gloved or ungloved hands of the dental practitioner or hygienist during procedures in the mouth of a patient. In fact, dental practitioners, along with the dental hygienists, have been cautioned to protect themselves from infection by using sterile gloves and masks and to use protective glasses when practicing dentistry or other dental procedures on their patients. Very recently the rapid spread of the Hepatitus virus and the Acquired Immune Deficiency virus has caused significant concern among dental practitioners and hygienists. The American Dental Association and other professional organizations have strongly urged that dental practitioners and hygienists take additional steps to decrease the chance of spreading the disease through the use of non-sterile implements.

It is therefore an object of the present invention to provide a protective covering, shield or barrier for the dental tray or bracket table handles or adjusting means to significantly reduce or prevent the spread of contagious, communicable diseases.

It is a further object of the present invention to provide such a shield or barrier which is disposable after a single use and which is easily applied and removed so that it will have wide-spread acceptance in the dental professions.

It is another object of the present invention to provide such a shield or barrier which is highly elastic and stretchable, yet tear resistant, and which is capable of covering the entirety of a variety of different shaped dental tray or bracket table handles.

Other objects will appear hereinafter.

SUMMARY OF THE INVENTION

The dental tray or bracket table handle or adjusting means covering, shield or prophylactic of the present invention is comprised of a thin, tear-resistant, semi-rigid but elastic material which is disposable for covering the exposed surfaces of each of several different types of dental tray or bracket table handles or adjusting means.

The present invention is an apparatus for significantly reducing or preventing the spread of communicable diseases which may be transmitted by or through contact with human body fluids and tissues during dental procedures. The apparatus comprises a removable, disposable, covering, shield or prophylactic for placement over and in proximate contact with a dental tray or bracket table handle or adjusting means. The shield is used to significantly reduce the spread of communicable diseases during a first and subsequent uses of the dental tray or bracket table handle or adjusting means in conjunction with the treatment of two or more patients.

The shield or prophylactic is comprised of a pocket portion for fitting over the dental tray or bracket table adjusting means and a collar portion for maintaining the shield in position on said adjusting means. The pocket portion is substantially hemispheric in shape having rounded ends and a single aperture or opening with said collar portion substantially surrounding said aperture or opening. The collar portion may have a rim providing a semi-rigid opening for maintaining the sterile integrity of the shield about the opening. The shield may be made from a thermoplastic, vinyl, latex, rubber, elastomeric, or other polymer-type material, natural or man-made, or any combination thereof. The material used is preferred to exhibit sufficient deformability, tear-resistance and material memory to withstand pulling and stretching during application and removal. Additionally, asceptic medicaments or talc may be applied to the internal surface of the shield to continue disinfection and to provide a means of lubricating the shield for ease in application and removal.

The shield or prophylactic of the present invention may also be constructed to exhibit a medium to high degree of frictional contact on its outer surface.

BRIEF DESCRIPTION OF THE DRAWINGS

For the purpose of illustrating the invention, there are shown in the drawings forms which are presently preferred; it being understood, however, that the invention is not limited to the precise arrangement and instrumentalities shown.

FIG. 1 is an isometric view of the shield or prophylactic of the present invention, with an elongated, larger version shown in phantom.

FIG. 2 is a perspective view of one type of dental tray or bracket table having two handles or adjusting means showing the shield or prophylactic of the present invention applied to the handles or adjusting means.

FIG. 3 is a perspective view of another type of dental tray or bracket table having two handles or adjusting means showing the shield or prophylactic of the present invention fully applied to the handles or adjusting means.

FIG. 4 is a perspective view of another type of dental tray or bracket table having two handles or adjusting means showing the shield or prophylactic of the present invention fully applied to the handles or adjusting means.

DETAILED DESCRIPTION OF THE INVENTION

The following detailed description is of the best presently contemplated modes of carrying out the present invention. This description is not intended in a limiting sense, but is made solely for the purpose of illustrating the general principles of the invention.

Referring now to the drawings in detail, wherein like numerals represent like elements, there is shown in FIG. 1 a shield or prophylactic 10 of the present invention. The shield 10 has an elongated hemispherical pocket portion 12 for fitting over the handles or adjusting means of various dental trays or bracket table. The pocket portion 12 has a single aperture or opening and is required to have rounded ends to fit tightly over the handles or adjusting means of the dental trays or bracket tables. Surrounding this aperture or opening is a collar portion 14. The collar portion 14 extends over the handles or adjusting means of the dental trays or bracket table for a nominal distance creating suspended membranes on both sides of the handles or adjusting means and terminates in a rolled portion or rim 16 at its distal end. The rim 16 provides a semi-rigid terminus for the shield 10 having a greater elastic memory for maintaining a snug fit on the handles or adjusting means of the various dental trays or bracket table, and the sterile integrity of the shield.

The handles or adjusting means of a dental tray or bracket table are manipulated by the dental practitioner, dental hygienist, or other member of the staff during dental procedures to accommodate the placement of the tray or bracket table in relation to the work area and the dental practitioner's or hygienist's body. The dental practitioner or hygienist will usually make adjustments to the placement of the tray or bracket table more than once while examining or working within a patient's mouth. It is usual to readjust the tray or bracket table several times during an examination or dental procedure, especially if the examination or procedure is lengthy. The readjustment is accomplished by grasping one or the other of the handles or adjusting means and physically moving the tray or bracket table. If the gloved or ungloved hand of the dental practitioner or other member of the staff had contacted infected tissue or body fluid, or just plain bacteria normally found within the mouth of a human and then contacted the handles or adjusting means to reposition the tray or bracket table, the handles or adjusting means have become non-sterile by such contact. The chance of passing such bacteria, or virus form, to another patient during a subsequent treatment of such patient without complete sterilization of the handles or adjusting means of the tray or bracket table is significant and highly probable.

The shield or prophylactic 10 of the present invention may be applied to the tray or bracket table handles or adjusting means of various tray or bracket table types by sliding the shield 10 over one end of a handle or adjusting means and stretching the shield 10 over the other end of the handle or adjusting means. Referring now to FIGS. 2, 3 and 4, the shield 10 is shown applied to the handles or adjusting means of various types of trays or bracket tables.

In FIG. 2 the shield 10 is shown stretched over each of two bar-type handles or adjusting means 122, 124 of one type of dental tray or bracket table 120. The tray or bracket table 120 is supported from the dental chair frame (not shown) by a support arm 126. The tray or bracket table 120 is attached to the support arm 126 at a pivot point beneath the tray or bracket table which is rigidly connected to the bar-type handles or adjusting means 122, 124 below. The tray or bracket table 120 has sides extending upward a short distance to contain the tools and implements placed thereon and to keep them from falling or rolling off. On the front of the tray or bracket table 120 receptacles 128 are attached to hold dental tools such as high speed drills, etc.

Upon application, the pocket portion 12 and the collar portion 14 of the shield 10 conform to the shape of, and completely cover the bar-type handles or adjusting means 122, 124. The pocket 12 and collar 14 of the shield 10, as they are stretched over the ends of the bar-type handles or adjusting means 122, 124, form a suspended membrane on either side of the handles or adjusting means 122, 124. The rim 16 of the shield 10 creates a snug fit about the handles or adjusting means 122, 124 maintaining the shield 10 in position until removal. Thus, the disinfected condition of the tray or bracket table 120 can be maintained by the timely application and removal of the shield 10.

In similar fashion to the tray or bracket table 120 just described, the shield 10 may also be applied to the tray or bracket table 220 of FIG. 3. The shield 10 is shown stretched over each of two C-shaped handles or adjusting means 222, 224 of another type of tray or bracket table 220. The tray or bracket table 220 is supported from the dental chair frame (not shown) by a support arm 226. The tray or bracket table 220 is attached to the support arm 226 at a pivot point permitting both the tray 220 and the bracket table 230 above to pivot at the end of the support arm 226 in unison and in fixed relation to each other. Distending downward from either end of the table 230 and rigidly connected thereto are two C-shaped handles or adjusting means 222, 224. The tray 220 has sides extending upward a short distance to contain the tools and implements placed thereon and to keep them from falling or rolling off. On the front of the table 230 receptacles 228 are attached to hold dental tools such as high speed drills, etc.

Also upon application, the pocket portion 12 and the collar portion 14 of the shield 10 conform to the shape of, and completely cover the C-shaped handles or adjusting means 222, 224. The pocket 12 and collar 14 of the shield 10, as they are stretched over the ends of the C-shaped handles or adjusting means 222, 224, form a suspended membrane on either side of the handles or adjusting means 222, 224. The rim 16 of the shield 10 creates a snug fit about the handles or adjusting means 222, 224 maintaining the shield 10 in position until removal. Thus, the disinfected condition of the tray 220 and table 230 can be maintained by the timely application and removal of the shield 10.

Likewise, the tray or bracket table 320, as shown in FIG. 4, can be similarly protected. The shield 10 may be applied to the tray or bracket table 320 by being stretched over each of two C-shaped handles or adjusting means 322, 324 of another type of tray or bracket table 320. The tray or bracket table 320 is supported from the dental chair frame (not shown) by a support arm 326. The tray or bracket table 320 is attached to the support arm 326 at a pivot point beneath the tray or bracket table 320 permitting freedom of movement about the centrally located pivot point. Appended from either end of the tray or bracket table 320 and rigidly connected thereto are two C-shaped handles or adjusting means 322, 324. The tray 320 has sides extending upward a short distance to contain the tools and implements placed thereon and to keep them from falling or rolling off. On the front of the tray or bracket table 320 receptacles 328 are attached to hold dental tools such as high speed drills, etc.

Upon application, the pocket portion 12 and the collar portion 14 of the shield 10 conform to the shape of, and completely cover the C-shaped handles or adjusting means 322, 324. As with the other trays, the pocket 12 and collar 14 of the shield 10, as they are stretched over the ends of the C-shaped handles or adjusting means 322, 324, form a suspended membrane on each side of the handles or adjusting means 322, 324. The rim 16 of the shield 10 creates a snug fit about the handles or adjusting means 322, 324 maintaining the shield 10 in position until removal. Thus, the disinfected condition of the tray or bracket table 320 can be maintained by the timely application and removal of the shield 10.

The shield 10 may be formed from a thermoplastic, vinyl, latex, rubber elastomeric or other polymer-type material, or any combination thereof, natural or manmade, which exhibits sufficient deformability to conform to the particular shape of and to stretch over the dental tray or bracket table handles or adjusting means of the several different types of trays or bracket tables (122 and 124, 222 and 224, 322 and 324). The material should also exhibit sufficient toughness and/or tear-resistance to withstand pulling and stretching during application and/or removal and sufficient material memory to return to and/or retain its original size and shape after application and/or removal. The shield 10 may also be formed with a larger aperture or pocket 12 to extend over longer handles or adjusting means of different tray or bracket table types. The phantom portion of the drawing of FIG. 1 is intended to indicate the larger version of the shield 10. The outer surface of the shield 10 is preferred to have a medium to high degree of frictional contact to provide sufficient firmness of grasp during dental procedures where hands, gloved or ungloved, may be wet or damp from body fluids or otherwise. To further the efforts to maintain a substantially sterile environment about the tray or bracket table, asceptic medicaments and talc may be applied to the internal surface of the shield 10 for continued disinfection and lubrication in the application and renewal of the shield.

In use, the shields are applied to the handles or adjusting means of the dental tray or bracket table after disinfection procedures are performed and before the beginning of an examination or other dental procedure on a patient. When the examination or other work on the patient is completed and before the next patient is examined, the shields are removed and discarded in a manner in accordance with government regulations for such solid refuse.

The shield or prophylactic 10 of the present invention can be used with all types of dental tray or bracket table handles or adjusting means due to its ability to adapt and/or conform to the variety of exterior shapes of the various handles or adjusting means. The present invention provides a significant step forward in reducing the rapid spread of contagious, communicable diseases of the Hepatitus and Acquired Immune Deficiency viral type which are borne on the body fluids and tissues of humans. The shield or prophylactic 10 provides a covering or barrier surface on the exterior of a dental tray or bracket table handle or adjusting means which, without the shield, would be a likely place for the harboring and transmittance of the diseases.

The present invention may be embodied in other specific forms without departing from the spirit or essential attributes thereof and, accordingly, reference should be made to the appended claims, rather than to the foregoing specification, as indicating the scope of the invention.

We claim:

1. A removable disposable dental tray or bracket table shield or prophylactic for placement over and in proximate contact with the means for adjusting the positioning or placement of said dental tray or bracket table for significantly reducing the spread of communicable diseases which may be transmitted by or through contact with human body fluids and tissues during a first and subsequent uses of the dental tray or bracket table and its adjusting means in conjunction with the treatment of two or more patients comprising a pocket portion for fitting over the dental tray or bracket table adjusting means and a collar portion for maintaining the shield in position on said adjusting means.

2. In accordance with claim 1 wherein said pocket portion is substantially hemispheric in shape having rounded ends and a single aperture or opening with said collar portion substantially surrounding said aperture or opening.

3. In accordance with claim 2 wherein said collar portion has a rim providing a semi-rigid condition about said opening for maintaining the sterile integrity of the shield about the opening.

4. In accordance with claim 1 wherein one or more additives selected from the group consisting of asceptic medicaments, talc, and lubricants are applied to the inner surface of the hemispherical and collar portions of the shield for continued disinfection and for lubrication in the application and removal of the shield.

5. In accordance with claim 1 wherein the outer surface of the shield has a medium to high degree of frictional contact.

6. In accordance with claim 1 wherein the shield is made from a material selected from the group consisting of thermoplastics, vinyls, latexes, rubbers, elastomerics, or other polymer-type materials, natural or man-made, or any combination thereof.

7. In accordance with claim 6 wherein said material exhibits sufficient deformability to stretch over the dental tray or bracket table adjusting means and toughness or tear-resistance to withstand pulling and stretching during application and removal and material memory to return to and retain its original size and shape after application and removal.

* * * * *